US00PP22661P2

(12) United States Plant Patent
Zerr

(10) Patent No.: US PP22,661 P2
(45) Date of Patent: Apr. 17, 2012

(54) POINSETTIA PLANT NAMED 'FISEARLTEZ'

(50) Latin Name: *Euphorbia pulcherrima*
Varietal Denomination: Fisearltez

(75) Inventor: Katharina Zerr, Höhr-Grenzhausen (DE)

(73) Assignee: Syngenta Crop Protection AG, Basel (CH)

( * ) Notice: Subject to any disclaimer, the term of this patent is extended or adjusted under 35 U.S.C. 154(b) by 120 days.

(21) Appl. No.: 12/658,860

(22) Filed: Feb. 16, 2010

(51) Int. Cl.
*A01H 5/00* (2006.01)

(52) U.S. Cl. ..... Plt./307

(58) Field of Classification Search ..... Plt./307
See application file for complete search history.

(56) References Cited

OTHER PUBLICATIONS

GTITM UPOVROM Citation for 'Fisearltez' as per DE PBR EUP00236; Dec. 22, 2008.*

* cited by examiner

*Primary Examiner* — Kent L Bell
(74) *Attorney, Agent, or Firm* — S. Matthew Edwards

(57) ABSTRACT

A new Poinsettia plant named 'Fisearltez' particularly distinguished by the red bracts with moderate lobing, relatively large flat, rosette-like inflorescences, dark green foliage, early flowering, and a medium sized plant habit.

1 Drawing Sheet

Latin name of the genus and species of the plant claimed: *Euphorbia pulcherrima.*

Varietal denomination: 'Fisearltez'.

BACKGROUND OF THE NEW PLANT

The present invention comprises a new Poinsettia, botanically known as *Euphorbia pulcherrima,* and hereinafter referred to by the variety name 'Fisearltez.'

'Fisearltez' is a product of a planned breeding program. The new cultivar has red bracts with moderate lobing, relatively large flat, rosette-like inflorescences, dark green foliage, early flowering, and a medium sized plant habit.

'Fisearltez' originates as a naturally occurring whole plant mutation discovered by the breeder in a flowering trial of the parent variety 'Fiscor,' U.S. Plant Pat. No. 9,364, in late 2000 in Dorsten, Germany. 'Fisearltez' was further examined and asexually propagated, by terminal tip cuttings, starting in the spring of 2001. As the flowering response may be influenced by many factors, the resulting plant was trialed and examined for stability through several years in the annual fall trial cultivation. The characteristics of 'Fisearltez' are firmly fixed and retained through successive generations of asexual reproduction.

BRIEF SUMMARY OF INVENTION

'Fisearltez' has not been observed under all possible environmental conditions. The phenotype may vary significantly with variations in environment such as temperature, light intensity and day length.

Plant Breeder's Rights for this cultivar were applied for in Canada on Feb. 11, 2009 and in Germany on Dec. 22, 2008. 'Fisearltez' has not been made publicly available more than one year prior to the filing of this application.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

The accompanying photographic drawing shows typical flower and foliage characteristics of 'Fisearltez' with colors being as true as possible with an illustration of this type. The photographic drawing shows a flowering potted plant of the new variety, taken in November 2008 and shows a 19-20 week old plant.

DETAILED BOTANICAL DESCRIPTION

The measurements were taken in in Hillscheid, Germany, latitude 50° north, on Dec. 10, 2009 on about 20 week old plants that were grown on benches in a greenhouse. Cultivation of these plants had started in late July 2009 with planting rooted cuttings in 14 cm pots and pinching about 2 weeks later. The plants were grown under natural day light in the fall (no black cloth used to initiate earlier flowering) and at the moderately warm temperature of 18° C. for the bench heating.

Color references are made to The Royal Horticultural Society Colour Chart (R.H.S.) 2001.

*TABLE 1*

DIFFERENCES BETWEEN THE NEW VARIETY 'FISEARLTEZ' AND A SIMILAR VARIETY

| | 'Fisearltez' | 'Fiscor' (U.S. Plant Pat. No. 9,364) |
|---|---|---|
| Flowering response: | 7-10 days earlier | 7-10 days later |
| Inflorescence size: | Larger | Usually smaller |
| Cyathia development: | More developed | Less developed |
| Plant size: | Somewhat smaller | Somewhat taller |

Plant:

*Form, growth and habit.*—Low shrub, self-branching, with robust stems slanting upward and outward.

*Plant height* (*inflorescence included*).—19-20 cm.

*Plant width.*—40-42 cm.

Roots:

*Number of days to initiate roots.*—Approximately 18-20 days at about 24 degrees C.

*Number of days to produce a rooted cutting.*—24-26 at 22 degrees C.

*Type.*—Fine, fibrous, free branching.

*Color.*—RHS N155B but whiter.

Foliage:

*Arrangement.*—Alternate.

*Quantity.*—5-6 leaves per branch.

*Aspect.*—Petioles and leaf blades are horizontally directed or show slightly downwards.

*Immature, leaf color, upper surface.*—RHS 137D.

*Lower surface.*—RHS 143B.

*Mature, leaf color, upper surface.*—Between RHS 137A and RHS 139A.

*Lower surface.*—RHS 137C.

*Length.*—12-13 cm.

*Width.*—8.3-9.5 cm.

*Shape.*—Ovate.

*Base shape.*—Most often obtuse.

*Apex shape.*—Acuminate.

*Margin.*—Entire with weak lobing; lobes usually have rounded tips.

*Texture, upper surface.*—Flat and smooth, apart from the protruding veins in a pinnate pattern.

*Lower surface.*—Glabrous.

*Color of veins, upper surface.*—RHS 179A to RHS 180A.

*Color of veins, lower surface.*—RHS 180D to RHS 181D.

*Petiole color, upper surface.*—RHS 53A or RHS 185A.

*Petiole color, lower surface.*—RHS 53D to RHS 184C.

*Petiole length.*—About 6-8 cm.

*Petiole diameter.*—0.3 cm.

*Petiole texture.*—Smooth and glabrous on both sides.

Stem:

*Color of stem.*—RHS 143B ground color, with upper portions may have an infusion of anthocyanins of about RHS 183D.

*Length of stem.*—About 16-18 cm.

*Diameter.*—0.6-0.8 cm.

*Length of internodes.*—1.5-3.0 cm.

*Texture.*—Glabrous.

Inflorescence:

*Type.*—Terminal cyme with surrounding whorl of colored bracts.

*Flowering, botanically* (*opening of the stamen, shedding of pollen*).—Late November.

*Start of flowering, commercially* (*sufficiently colored bracts*).—Mid to late November.

*Flowering response time.*—About 8 weeks from equinox.

*Duration of flowering.*—4-8 weeks.

*Lastingness of the inflorescence.*—6-10 weeks.

*Fragrance.*—Absent.

*Shape of inflorescence.*—Rosette-like arrangement, nearly flat, horizontally borne.

*Diameter of inflorescence.*—23-27 cm.

*Inflorescence, vertical diameter.*—2.5-4.0 cm.

*Number of completely colored bracts per inflorescence* (*sized over 2 cm*).—10-14.

*Single bract, shape.*—Ovate, with moderate lobing.

*Bract, apex.*—Acuminate.

*Bract, base.*—Rounded or obtuse.

*Bract margin.*—Entire.

*Single bract, length of blade.*—12.5 cm, younger bracts diminishing in size.

*Single bract, width of blade.*—8.8 cm.

*Bract color, upper side.*—RHS 46B.

*Bract color, lower side.*—*Between RHS*46B and 46C, or RHS 53C.

*Vein color, upper surface.*—Indistinct, similar as bract blade.

*Vein color, lower surface.*—From RHS 50C to RHS 180D.

*Texture.*—Flat, smooth or somewhat rugose.

*Bract petiole length.*—About 1.0-2.0 cm.

*Bract petiole diameter.*—0.3 cm.

*Petiole color, upper surface.*—RHS 46A to RHS 46B.

*Petiole color, lower surface.*—RHS 50C.

Cyme (true inflorescence):

*Cyme, diameter.*—2-2.5 cm.

*Number of cyathia.*—About 15, borne in a small cluster.

*Cyathium, shape.*—Ovate.

*Cyathium, diameter.*—0.5 cm.

*Cyathium, length.*—0.5-0.6 cm.

*Cyathium, color.*—Mainly RHS 143C, top is RHS 46B.

*Peduncle length.*—0.2-0.3 cm.

*Peduncle diameter.*—0.2-0.3 cm.

*Peduncle color.*—RHS 144C to 145A.

*Peduncle texture.*—Smooth, glabrous.

*Nectar cups.*—Usually one, emerging from the outer (abaxial) surface of the cyathium.

*Nectar cup,* (*vertical*) *length.*—About 0.2-0.4 cm.

*Nectar cup, horizontal diameter.*—Most often 0.5 cm in length, 0.2-0.3 cm wide.

*Nectar cup, color.*—RHS 13A to RHS 21A.

Reproductive organs:

*Stamen* (*actually reduced male florets*).—Usually in a bunch of 10-20 at the top of the cyathium.

*Shape.*—Strap-like.

*Filament length.*—0.3-0.4 cm.

*Filament color.*—RHS 46B.

*Anther color.*—RHS 11A.

*Anther diameter.*—0.1 cm.

*Pollen quantity.*—Moderate (normal quantity for the species).

*Pollen color.*—RHS 12A.

*Pistils* (*actually female flowers*).—Usually sparse in late crops, occurrence depends much on light intensity, appears (if at all) about 4 weeks later than the stamen.

*Number of pistils.*—One per cyathium.

*Stigma shape.*—Trifurcate, 6-lobed.

*Stigma color.*—RHS 46A.

*Style color.*—RHS 46B.

*Style length.*—0.3 cm.

*Ovary shape.*—Ovate to obovate, 3 ovules.

*Ovary size.*—0.5 cm in diameter, but increasing.

*Ovary color.*—RHS 143B.

Fertility/seed set:

*Seed pods.*—Obovate and 3-cornered, about 1.8 cm in length and 1.5 cm in diameter; 3 seeds.

*Seed grains.*—Resemble peas both in size and appearance, round, 0.6 cm in diameter.

Disease/pest resistance: Disease/pest resistance has not been observed on this hybrid.

What is claimed is:

1. A new and distinct variety of Poinsettia plant named 'Fisearltez,' substantially as illustrated and described herein.

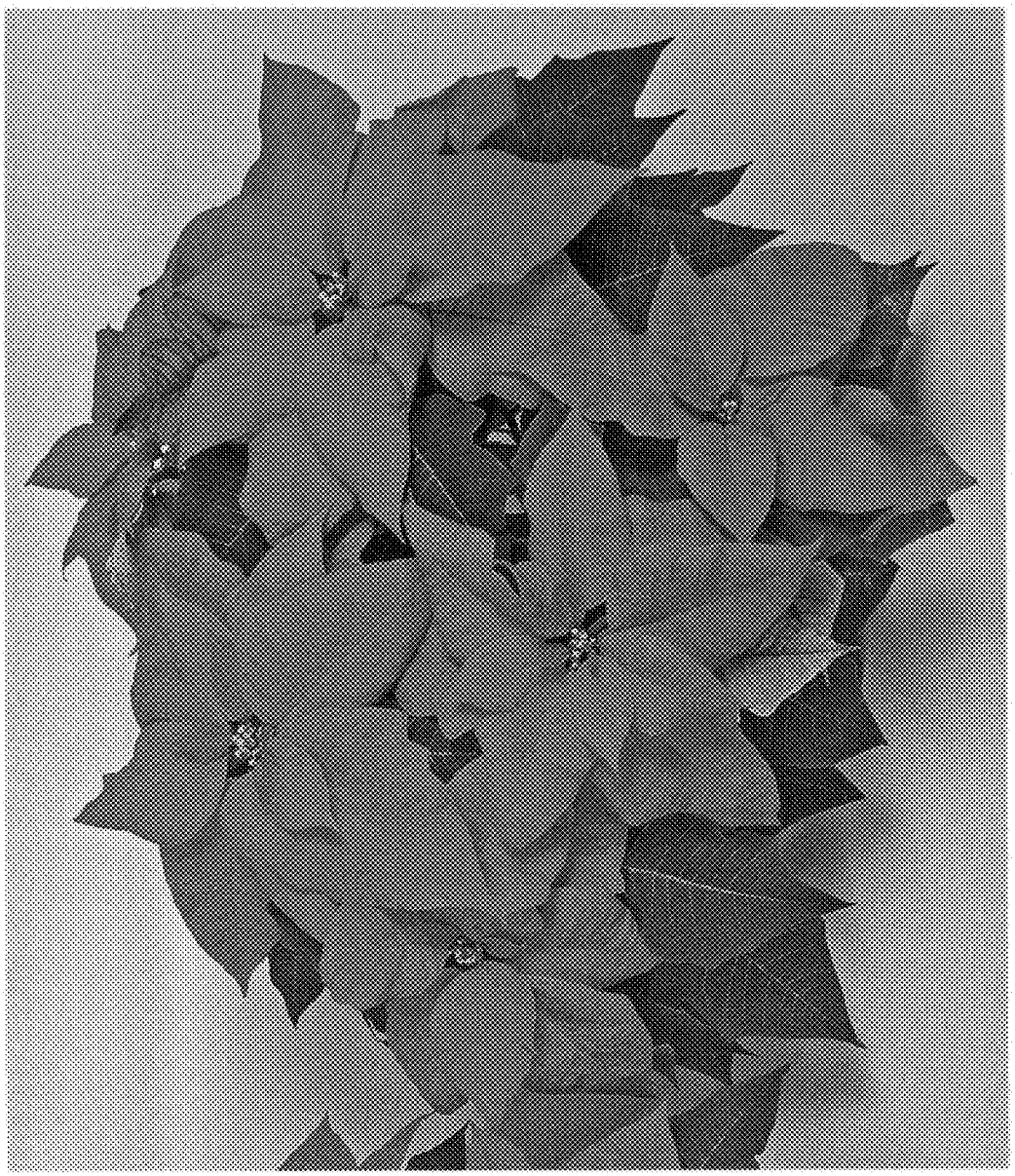

* * * * *